United States Patent [19]

Barnes et al.

[11] 4,003,790
[45] Jan. 18, 1977

[54] NITROGEN CONTROL IN MIXED CULTURE PRODUCTION

[75] Inventors: Lionel J. Barnes, Ashford; John H. Harwood, Stoke-on-Trent; David E. F. Harrison; Harmannus J. Doddema, both of Faversham, all of England

[73] Assignee: Shell Oil Company, Houston, Tex.

[22] Filed: Aug. 11, 1975

[21] Appl. No.: 603,416

[30] Foreign Application Priority Data

Aug. 12, 1974 United Kingdom ............ 35435/74

[52] U.S. Cl. .............................. 195/28 R; 195/49; 195/96; 195/111
[51] Int. Cl.² ......................................... C12B 1/00
[58] Field of Search ............ 195/28 R, 111, 50, 49, 195/96, 115, 118, 123, 65, 66 R

[56] References Cited

UNITED STATES PATENTS 3,816,252   6/1974   Moran et al. ............ 195/117

FOREIGN PATENTS OR APPLICATIONS 45-36156   1970   Japan ............ 195/111

Primary Examiner—R. B. Penland

[57] ABSTRACT

Use of urease positive micro-organisms to form ammonium-ions in a process for the culture of hydrocarbon-utilizing micro-organisms.

4 Claims, No Drawings

NITROGEN CONTROL IN MIXED CULTURE PRODUCTION

BACKGROUND OF THE INVENTION

This invention relates to a process for the production of micro-organisms. Many micro-organisms are known which can utilise hydrocarbons as their carbon and/or energy source. The dried biomass obtainable by the cultivation of such micro-organisms, often referred to as single cell protein, is rich in protein and can be used as a possible food-stuff or food supplement for man and animals.

A process for the cultivation of hydrocarbon-utilising micro-organisms usually comprises the growth of such organisms under aerobic conditions in a liquid growth medium comprising, in addition to the carbon source, assimilable sources of nitrogen, such as nitrogen ($N_2$) gas, nitrate-ions, ammonium-ions or urea. Although nitrogen gas is cheaply available the use thereof as source of nitrogen is disadvantageous in that much energy is required to metabolise it which makes it rather expensive on the carbon-source utilised by the micro-organisms. Nitrate-ions are also expensive on the carbon source as they have to be reduced to ammonium-ions in order to become metabolisable by the micro-organisms. Ammonium-ions are both cheaply available and not expensive on the carbon-source but have the draw-back of being inhibitory to the growth of many organisms, particularly certain methanol- and methane-utilising bacteria, when being present in the liquid growth medium in too high a concentration. Finally urea, which is also cheaply available and is not expensive on the carbon-source, can only be utilized by a restricted number of bacterial species.

It is an object of the present invention to provide an improved process for the cultivation of hydrocarbon-utilising micro-organisms whereby the disadvantages inherent in the use of certain sources of nitrogen are overcome.

SUMMARY OF THE INVENTION

Accordingly the invention provides a process for the production of micro-organisms in which one or more hydrocarbon-utilising micro-organism(s) is/are grown under aerobic conditions in a liquid growth medium comprising urea and essential mineral salts in the presence of a hydrocarbon and in the presence of one or more non-hydrocarbon utilising urease positive micro-organism(s) which is/are capable of metabolising organic substances produced by the growing hydrocarbon-utilising micro-organism(s).

The term "hydrocarbon" as used herein is meant to include not only hydrocarbons, but also oxygenated derivatives thereof.

The term "micro-organism" is used herein in a broad sense to include not only bacteria, but also yeasts, filamentous fungi, actinomycetes and protozoa.

According to the process of the invention the urease positive micro-organisms gradually break down urea thereby forming ammonium-ions in the liquid growth medium which ions become then available to the hydrocarbon-utilising micro-organisms as an easily assimilable source of nitrogen. One of the advantages of the process of the invention is the face that the ammonium ions become available to the hydrocarbon-utilising micro-organisms whilst the concentration thereof is checked by the non-hydrocarbon-utilising urease positive micro-organisms thus preventing the formation of inhibitory concentrations of ammonium ions in the liquid growth medium.

When the hydrocarbon-utilising micro-organisms grow quickly the rate of production of extracellular products is high and consequently the rate of growth of the non-hydrocarbon-utilising urease positive micro-organisms, which metabolize these extracellular products, is high. Therefore, the latter micro-organisms are able to break down the supplied urea into ammonium ions at a fast rate and thus ammonium ions are available to the hydrocarbon-utilising organisms at a fast rate to suit their fast growth.

When the hydrocarbon-utilising organisms grow slowly, however, the rate of production of extracellular products is low and consequently the rate of growth of the non-hydrocarbon utilising urease positive micro-organisms is low. Therefore, the latter micro-organisms are unable to break down the supplied urea into ammonium ions at a fast rate. This low rate of production of ammonium ions matches the slow growth rate of the hydrocarbon-utilising micro-organisms.

Thus ammonium ions are available to the hydrocarbon-utilising micro-organisms at a rate proportional to the requirement, i.e. proportional to the growth rate of the hydrocarbon-utilising micro-organisms. Consequently the concentration of the ammonium ions in the liquid growth medium remains relatively constant and in practice will virtually never exceed the level at which inhibitory effects on growth occur.

In its simplest form the culture of micro-organisms used in the process of the invention comprises a hydrocarbon-utilising micro-organism which cannot normally utilise urea but can utilise ammonium ions as nitrogen source, together with one or more urease positive non-hydrocarbon-utilising species which can break down urea and release ammonium ions into the medium.

The hydrocarbon-utilising micro-organism preferably is a methane-utilising bacterium which grows in the presence of methane or a methanol-utilising bacterium which grows in the presence of methanol. Good results are obtained if the culture contains both a methane-utilising bacterium and a methanol-utilising bacterium and is grown in the presence of methane.

However, other micro-organisms may also be present in the culture, for example one or more non-hydrocarbon-utilising urease negative micro-organism(s) which is/are capable of metabolising organic substances produced by the growing hydrocarbon-utilising micro-organism(s), and also further hydrocarbon-utilising micro-organism may be present.

Methane-utilising micro-organisms which can suitably be used in the process of the invention are for example *Methylococcus capsulatus, Methylococcus minimus, Methylobacter vinelandii, Methylosinus trichosporium, Methylocystis parnis* and the organism $SM_3$ (NCIB 11084) which has been described in detail in U.S. patent application Serial No. 539,202. Suitable methanol-utilising micro-organisms are for example *Hyphomicrobium sp.* (NCIB No. 11040), *Pseudomonas extorquens, Pseudomonas methylotropha (NCIB Nos. 10,508 – 10,515 and 10,592 – 10,596)* and the organism OML (NCIB 11112) which has been fully described in U.S. pat. application Ser. No. 539,202. Any non-hydrocarbon-utilising bacterium capable of utilising urea and capable of growing in mixed culture with hydrocarbon-utilising bacteria may be used, for example the organisms $M_1$ (NCIB 11062), $M_2$ (NCIB 11061) and $M_4$ (NCIB 11065) which have all been fully described in U.S. pat. application Ser. No. 539,202. A preferred mixed culture for use in the process of the invention in the presence of methane is the culture designated T3 (NCIB 11085) which comprises the methane-utilising micro-organism SM3 (NCIB 11084), the methanol-utilising micro-organism OML (NCIB 11112) and four non-methylotrophic micro-organisms $M_1$, $M_2$, $M_4$ and $M_3$ (NCIB 11063). $M_3$ is a urease negative micro-organism. The culture $T_3$ and its components have been fully described in U.S. pat. application No. 539,202, and are characterized as follows:

MICROBIOLOGICAL CHARACTERISTICS OF THE CULTURE T3

1. the culture consists of an obligate methane-utilising bacterium designated SM3 (NCIB 11084) growing in association with a methanol utilising bacterium and species of non-methylotrophic bacteria. The methane-utilising organism SM3 (NCIB 11084) has a somewhat variable morphology, appearing as short rods or cocci rods, and has an internal membrane structure arranged in parallel stacks in the cell. This organism grows only weakly alone on methane. On the basis of the above description the organism appears to be a previously undescribed species of a Methylomonas type (NCIB 11084).

2. The methanol-utilising organism designated OML (NCIB 11112) is characterised by its ability to grow and form colonies only on agar plates containing methanol as the sole carbon source. No growth occurs in the presence of glucose, lactose, sucrose, mannitol, inositol, citrate or nutrient agar. The organism is approximated $2\mu$ long and $1\mu$ wide, with a single polar flagellum. Colonies on agar are smooth and grey with an entire margin, appearing on methanol/mineral salts agar plates after incubation for 2 days at 42° C. On the basis of the above description the organism appears to be a previously undescribed species of Pseudomonas type (NCIB 11112).

3. Other types of organism were isolated from the mixture which would grow neither on methane nor methanol as the only carbon source. These were designated $M_1$, $M_2$, $M_3$ and $M_4$. These were submitted to standard tests in order to determine to which general of micro-organisms they belonged.

The results of these tests are shown in Tables 1 and 2.

From the results of these tests the following conclusions can be drawn as to the identity of the organisms:

Organism $M_1$ is a species of Pseudomanas (NCIB 11062).

Organism $M_2$ is a species of Mycobacterium (NCIB 11061).

organism $M_3$ is a species of pseudomonas (NCIB 11063).

Organism $M_4$ is a species of Pseudomonas (NCIB 11065).

TABLE 1

IDENTIFICATION OF NON-METHANE UTILISING BACTERIA PRESENT IN MIXED CULTURE T3 — FIRST STAGE TESTS

| TEST | $M_1$ | $M_2$ | $M_3$ | $M_4$ |
|---|---|---|---|---|
| GRAM STAIN | − | + | − | − |
| SHAPE | rod | rod | rod | rod |
| SPORES FORMED | − | − | − | − |
| MOTILE | + (by means of polar flagella) | − | + (by means of polar flagella) | + (by means of polar flagella) |
| CATALASE PRODUCTION | + | + | + | + |
| OXIDASE ACTIVITY | + | − | + | + |
| GLUCOSE UTILIZATION (acid) | − | − | − | − |
| O - F test (Hugh & Leifson) | − | − | Oxidative | Oxidative |
| ACID FAST | | non-acid fast | | |

TABLE 2

IDENTIFICATION OF NON-METHANE UTILISING BACTERIA PRESENT IN MIXED CULTURE T3 — SECOND STAGE TESTS

| TEST | $M_1$ | $M_2$ | $M_3$ | $M_4$ |
|---|---|---|---|---|
| UREASE ACTIVITY | − | + | − | + |
| CITRATE UTILIZATION | + | − | + | + |
| GELATIN HYDROLYSIS | + | − | + | + |
| INDOLE PRODUCTION | − | − | − | − |
| MR (methyl red) & VP (Voges-Proskauer) REACTION | − | − | − | − |
| GLUCOSE (ACID PRODUCTION) | − | − | − | − |
| LACTOSE (ACID) | − | − | − | − |
| SUCROSE (ACID) | − | − | − | − |
| MANNITOL (ACID) | − | − | − | − |
| MALTOSE (ACID) | − | − | − | − |
| GROWTH ON NUTRIENT AGAR | + | + | + | + |
| CATALASE ACTIVITY | + | + | + | + |
| REDUCTION OF NITRATE | − | weak | weak | − |

Urea is suitably present in the liquid growth medium in a concentration from 3–50 g/l. It will be obvious that no substantial amounts of ammonium ions should be supplied to the liquid medium other than through the break down of urea.

Other elements which are usually present in the medium are phosphorous, sulphur, magnesium and iron. The phosphorus source is preferably one or more phosphates, for example $K_2HPO_4$, $KH_2PO_4$ or $Na_2HPO_4$ or phosphoric acid, preferably present in a concentration from 3–20 g/l. The sulphur source may be sulphuric acid or a sulphate suitably in a concentration from 0.5–5.0 g/l. The two metals are provided as one or other of their salts, for example $MgSO_4.7H_2O$ in a concentration from 0.2–2.0 g/l and $FeCl_3.6H_2O$ in a concentration from 0.01–0.1 g/l.

The medium may also contain trace amounts of other elements in the form of suitable salts, for example, calcium, manganese, zinc, cobalt, molybdenum and boron. An example of a suitable medium is given in the Example.

The process of the invention may be carried out batch-wise, semi-continuously but preferably in continuous flow culture. To obtain growth the micro-organisms are inoculated into the medium which is contacted with oxygen. For continuous flow culture the microorganisms may be grown in any suitably adapted fermentation vessel, for example a stirred baffled fermenter or sparged tower fermenter, which is provided either with internal cooling or an external recycle cooling loop. Fresh medium is pumped continuously into the culture at rates equivalent to 0.02 to 1.00 culture volumes per hour and culture is removed at a rate such that the volume of culture remains constant. Oxygen and possibly carbon dioxide is contacted with the medium preferably by bubbling continuously through a sparger at the base of the vessel. The source of oxygen for the culture may be air, oxygen or oxygen enriched air. Spent gas is removed from the head of the vessel. Spent gas may be recycled either through an external loop or internally by means of a gas inducer impeller.

The temperature of the culture is generally maintained between 30° to 50° C and preferably from 38° to 45° C. The pH of the culture is usually controlled at a pH between 6.0 and 8.0 and preferably between 6.4 and 7.4 by the appropriate addition of an alkali, for example NaOH, KOH, and/or an acid, for example $H_2SO_4$ or $H_3PO_4$.

The micro-organism cells may be harvested from the growth medium by any of the standard techniques commonly used, for example flocculation, sedimentation, and/or precipitation, followed by centrifugation and/or filtration. The biomass is then dried e.g. by freeze or spray drying and may be used in this form as a protein food stuff or food supplement for man or animals. The invention is illustrated further in the following Example.

EXAMPLE

A Biotec fermenter with a working volume of 2.5 litre was charged with medium and inoculated with 100 ml of culture T3 (comprising the bacteria SM3, OML, $M_1$, $M_2$, $M_3$ and $M_4$). This culture was prepared as described in our co-pending U.S. pat. application Ser. No. 539,202. The medium contained the following ingredients:

| | | |
|---|---|---|
| $KH_2PO_4$ | 1.6 | grams/liter |
| $Na_2HPO_4$ | 1.16 | " |
| Urea | 1.122 | " |
| $MgSO_4.7H_2O$ | 0.08 | " |
| $FeSO_4.7H_2O$ | 0.014 | " |
| $Ca(NO_3)_2.4H_2O$ | 0.025 | " |
| $CuSO_4.5H_2O$ | $8\times10^{-5}$ | " |
| $ZnSO_4.7H_2O$ | $6.8\times10^{-7}$ | " |
| $MnSO_4.4H_2O$ | $6.0\times10^{-7}$ | " |
| $Na_2MoO_4.2H_2O$ | $4.8\times10^{-7}$ | " |

The fermenter temperature was controlled at 42° C and the pH at 7.0. A methane (25%)/air (75%) mixture was bubbled into the base of the fermenter at a rate of 600 ml/min. The fermenter was stirred by means of a single 6 bladed impeller at 1200 rpm.

Growth occurred within 24 hours and when the dissolved oxygen tension reached zero, continuous culture was carried out, using medium of the above composition. The dilution rate was increased at intervals of about 2 hours by steps of about 0.02 $h^{-1}$ until a dilution rate of 0.175 $h^{-1}$ was reached.

The fermenter was then operated under the following conditions:

| | |
|---|---|
| Absolute inlet gas pressure | 770mmHg |
| Inlet gas temperature | 24° C |
| Measured inlet gas flow rate | 116.8 sec $l^{-1}$ |
| Inlet nitrogen (percentage) | 67.65 |
| Inlet methane (percentage) | 11.79 |
| Inlet carbon dioxide (percentage) | 0.50 |
| Inlet oxygen (percentage) | 20.06 |
| Outlet nitrogen (percentage) | 80.13 |
| Outlet methane (percentage) | 4.20 |
| Outlet carbon dioxide (percentage) | 6.08 |
| Outlet oxygen dioxide (percentage) | 9.59 |
| Liquid medium flow rate | 0.356 $lh^{-1}$ |
| Fermenter volume (liter) | 1.9 |
| pH | 7.1 |
| Biomass concentration | 3.22 $gl^{-1}$ |
| Agitation speed | 1380 rpm |
| Fermenter temperature | 41.8° C |

Under these conditions a methane-limited steady state was obtained. Analysis for urea and ammonium ions (expressed in $NH_3$) revealed the following information.

| | Concentration in the medium | Concentration in the culture |
|---|---|---|
| Urea | 1.122 $gl^{-1}$ | 0.250 $gl^{-1}$ |
| $NH_3$ | — | 0.051 $gl^{-1}$ |

Thus it can be seen that urea is utilized. Ammonium ions are released into the medium and are available to the methane-utilising bacteria as the nitrogen source. The level of ammonium ions in solution in the culture broth is low (51 mg $l^{-1}$) allowing good growth of the methane-utiliser with no inhibition. The total amount of residual nitrogen source in the culture, if it were in the form of ammonium ions, would be sufficient to inhibit growth and cause washout of the culture.

What we claim is:

1. A process for production of bacteria in which a methane-utilizing bacterium having the NCIB Accession No. 11084 is grown under aerobic conditions in a liquid growth medium comprising urea and essential minerals salts in the presence of methane and in the presence of (a) a methanol-utilizing bacterium having the NCIB Accession No. 11112 which is capable of metabolizing methanol produced by the bacterium having the NCIB Accession No. 11084 and (b) four non-hydrocarbon-utilizing bacteria having the NCIB Accession Nos. 11062, 11061 11063 and 11065 capable of metabolizing organic substances produced during the metabolism of methane and/ or methanol.

2. A process according to claim 1, wherein the methane-utilizing bacterium, the methanol-utilizing bacterium and the four non-hydrocarbon-utilizing bacteria are employed as the mixed culture designated T3 having the NCIB Accession No. 11085.

3. A process according to claim 2, wherein the temperature is maintained in the range 30°–50° C.

4. A process according to claim 2, wherein pH is controlled in the range 6.0 – 8.0.

* * * * *